United States Patent
Danzer et al.

(10) Patent No.: US 7,664,557 B2
(45) Date of Patent: Feb. 16, 2010

(54) MEDICAL APPARATUS AND METHOD

(75) Inventors: Uwe Danzer, Kalchreuth (DE); Robert Kagermeier, Nürnberg (DE); Judith Regn, Nürnberg (DE); Dietmar Sierk, Erlangen (DE); Reiner Staab, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 218 days.

(21) Appl. No.: 11/897,386

(22) Filed: Aug. 30, 2007

(65) Prior Publication Data

US 2008/0058967 A1    Mar. 6, 2008

(30) Foreign Application Priority Data

Aug. 31, 2006  (DE) .................. 10 2006 040 941

(51) Int. Cl.
*G05B 19/18*   (2006.01)
*A61N 1/00*    (2006.01)

(52) U.S. Cl. .............. 700/66; 700/56; 700/60; 700/61; 700/65; 607/60

(58) Field of Classification Search ............ 700/56, 700/60, 61, 65–66; 607/60
See application file for complete search history.

(56) References Cited

U.S. PATENT DOCUMENTS

| | | | |
|---|---|---|---|
| 5,526,245 A * | 6/1996 | Davis et al. ................. 362/233 |
| 6,078,947 A * | 6/2000 | Kagermeier ................. 709/203 |
| 6,785,578 B2 * | 8/2004 | Johnson et al. ............... 700/60 |
| 7,010,369 B2 * | 3/2006 | Borders et al. ................ 700/90 |
| 7,035,698 B2 * | 4/2006 | Johnson et al. ............... 700/59 |
| 2003/0069653 A1 | 4/2003 | Johnson et al. |
| 2004/0082852 A1 * | 4/2004 | Cherek et al. ............... 600/427 |
| 2005/0004630 A1 * | 1/2005 | Kagermeier et al. .......... 607/60 |
| 2005/0004688 A1 | 1/2005 | Johnson et al. |
| 2006/0203250 A1 * | 9/2006 | Regn et al. .................. 356/482 |
| 2006/0255904 A1 * | 11/2006 | Danzer et al. ................ 340/5.2 |
| 2007/0182729 A1 * | 8/2007 | Klingenbeck-Regn et al. ................ 345/418 |
| 2008/0150754 A1 * | 6/2008 | Quendt .................. 340/870.07 |

FOREIGN PATENT DOCUMENTS

DE     102 46 934 A1   4/2003

* cited by examiner

*Primary Examiner*—Ramesh B Patel

(57) ABSTRACT

To facilitate an intuitive operation of an adjustable device of a medical apparatus, a system for the automatic setting of an operating configuration of the portable control module controlling the adjustable device is provided. Different operating configurations regarding the directional control of the movement of the movable device differ are based on the relative spatial position of the adjustable device with respect to the control module. The system includes at least one signal sender unit for sending a signal. The signal sender unit may be arranged on the control module. The system further includes at least two signal converter units for converting and retransmitting or for converting and reflecting the signal. The signal converter units may be arranged on different positions on the device. A signal receiver unit is used for receiving the converted signal, and the receiver unit may be arranged on the control module.

16 Claims, 3 Drawing Sheets

MEDICAL APPARATUS AND METHOD

CROSS REFERENCE TO RELATED APPLICATIONS

This application claims priority of German application No. 10 2006 040 941.8 filed Aug. 31, 2006, which is incorporated by reference herein in its entirety.

FIELD OF THE INVENTION

The invention relates to a medical apparatus with an adjustable device and a portable control module and a method for the automatic setting of an operating configuration of a portable control module of a medical apparatus according to the claims.

BACKGROUND OF THE INVENTION

The provision of flexibly positionable and portable control modules which have operating elements for setting different system parameters to operate medical apparatuses, in particular x-ray systems, is known. Thus, such control modules enable the application of x-rays to be controlled or movable components of the x-ray equipment such as, for example, the patient couch or the C-arm to be moved.

The positioning of the control module is important for intuitive operation by an operator, especially when two or three-dimensional movements of movable components are being controlled. If, for example, the operator with the control module is standing in front of a mobile patient couch and moves a joystick on the control module out to the right, then the operator expects the patient couch to move in this direction. But this is only the case if the relative arrangement between the control module and the patient couch is known to the system controller and the control module is configured correspondingly. This is the reason why with portable control modules it is necessary for the operator to check and possibly perform a time consuming and complicated manual configuration of the control module when the x-ray apparatus is operated or every time there is a change in position.

SUMMARY OF THE INVENTION

The object of the present invention is to enable a simple intuitive operation in the case of a medical apparatus with an adjustable device and with a portable control module for the control thereof.

According to the invention the object is achieved by a medical apparatus and by a method for automatic calibration according to the independent claims; advantageous embodiments of the invention respectively form the subject matter of the subclaims.

The apparatus according to the invention allows intuitive and simple operation in that the operating configuration of the portable control module is automatically set by means of a system. Such a system advantageously has at least: one signal sender unit for sending a signal, which signal sender unit is arranged on the control module, at least two signal converter units for converting the signal arranged at different positions on the device, and a signal receiver unit for receiving the converted signal, which signal receiver unit is arranged on the control module. Such a system or the components of said system can be acquired easily and at a reasonable price, and implemented at little cost or energy in existing medical apparatuses.

The method according to the invention allows a signal to be sent out by the control module using simple means, converted by to the adjustable device position, reflected and received again in its converted form by the control module, wherein the converted response signal contains the information required to set the correct operating configuration. In this connection, different operating configurations of the control module can advantageously be set as a function of the converted signal.

According to one advantageous embodiment of the invention, the method is carried out automatically each time the medical apparatus or the control module is put into operation, so that right from the start a person using the medical apparatus can work intuitively regardless of his/her position. According to a further embodiment of the invention, the method is carried out automatically at regular time intervals. This ensures that a user who, for example, changes his/her position and that of the control module while the medical apparatus is in operation, also retains an intuitive operation.

According to further embodiments of the invention the adjustable device is formed by a patient table, in particular a patient table with an at least two-dimensionally adjustable tabletop, or by an adjustable C-arm.

In an advantageous manner, the signal sender unit and the signal receiver unit are formed by an RFID read device, a so-called reader and the signal converter units are each formed by one RFID transponder. The RFID technology is available, reasonably priced and perfected, and can, therefore, be used reliably and easily implemented.

According to a further embodiment of the invention, the signal sender unit is formed by an optical sender unit and the signal receiver unit is formed by an optical sensor. These components are also standard so that they are easily available and reasonably priced. In an advantageous manner, in conjunction with optical sensors, the signal converter units are formed by optically reflecting, diffracting or absorbing markings, in particular in the form of adhesive strips. Advantageously, differently reflecting, diffracting or absorbing markings are arranged on different sides of the movable device. Thus, for example, a different marking can be arranged on each of all four sides of the patient table.

It is especially advantageous to arrange the signal converter units so they can be detached. This allows them to be easily replaced should they become damaged or contaminated.

According to further embodiments of the invention, the portable control module is formed by a joystick or by a remote operating unit.

BRIEF DESCRIPTION OF THE DRAWINGS

The invention and other advantageous embodiments according to the features of the subclaims are explained in greater detail below, using schematic exemplary embodiments in the drawing, without this limiting the invention to these exemplary embodiments; shown are:

DETAILED DESCRIPTION OF THE INVENTION

Figure 1:
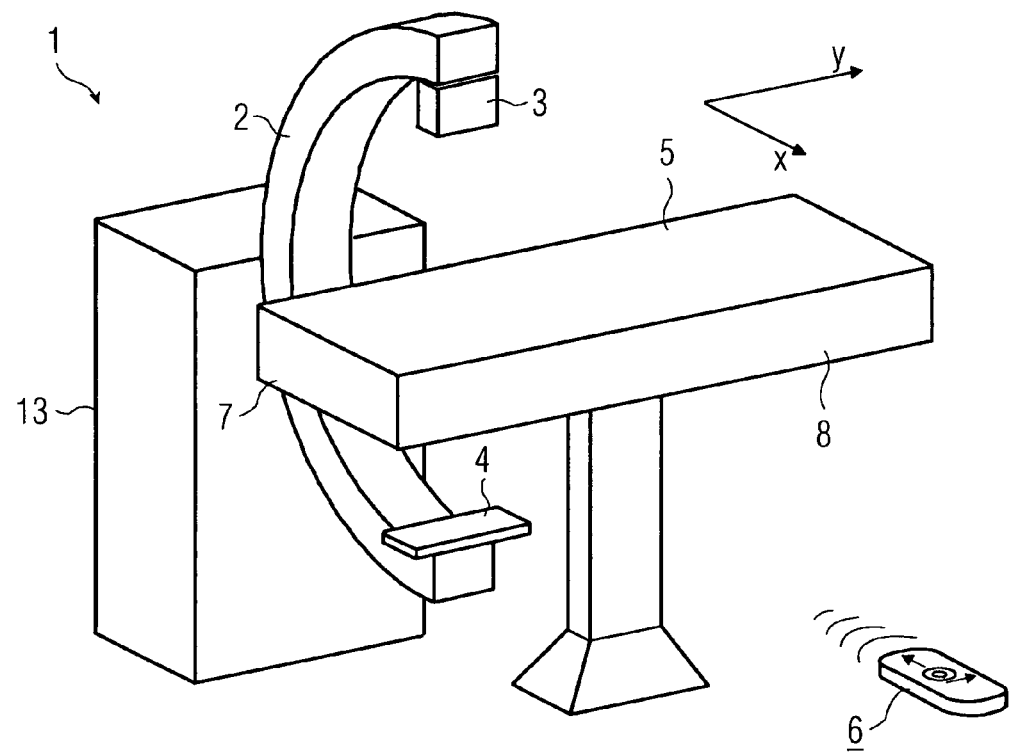
FIG. 1 a perspective view of a medical apparatus according to the prior art.

FIG. 1 shows a medical x-ray device 1, which has, as essential components, an adjustable C-arm 2, a system control device 13 and an assigned adjustable patient table 5. An x-ray source 3 is arranged at one end of the C-arm 2 in order to emit x-rays, an x-ray image recorder 4 is arranged at the opposite end of the C-arm, a digital flat image detector for example. For an x-ray image, a patient lying on the patient table 5 is x-rayed and the characteristically weakened x-ray is herewith transformed into electrical signals by the flat image detector and stored. The stored signals are then routed to the system control device 13, for example to an image system located in said control device, and processed or displayed.

The patient table 5 of the medical x-ray device 1 is adjustable in at least two spatial directions in its plane, toward the first spatial axis x and toward the second spatial axis y, which is orthogonal to the first spatial axis x. In addition, the patient table can be, for example, movable relative to its base, or be in its entirety mobile on rails. The adjustability can be controlled using a mobile, cable-free, known control module 6.

Figure 2:
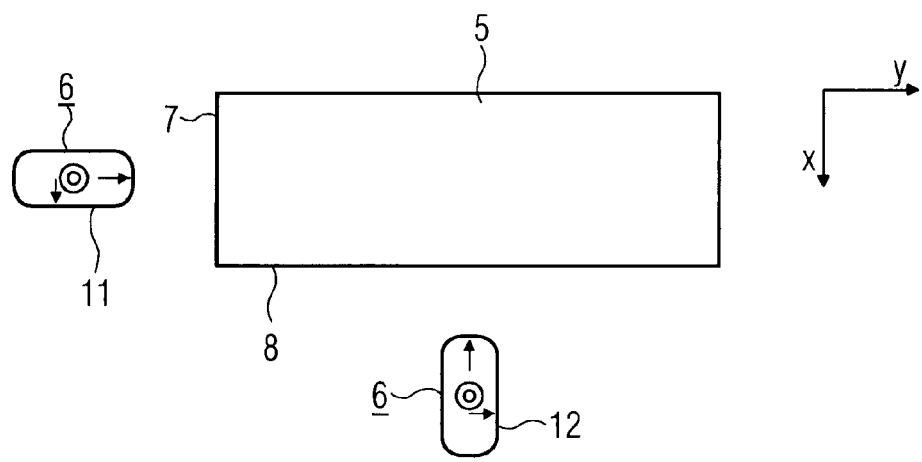
FIG. 2 a top view from above of an adjustable patient table and designated control modules.

With such systems according to the prior art, there is the problem that an operator who wishes to operate the control module intuitively in a first position 11, requires a different operating configuration with respect to the control of the patient table 5, than when said operator wishes to operate the known control module 6 intuitively in a second position 12—shown in FIG. 2. Operator intuitive operation is understood here to mean that the patient table 5 always moves in exactly the direction that the operator selects from his/her position; thus if the operator is standing at a first side 7 of the patient table 5 and enters right in the known control module 6, the operator expects the table also to move to the right as seen from his/her perspective; if the operator is standing at a second side 8 of the patient table 5, then said table should also move to the right as seen from his/her perspective.

To this end a system is provided for the automatic setting of an operating configuration of a portable control module, wherein different operating configurations in respect of the control of the movement of the movable device differ as far as the relative spatial position of the adjustable device to the control module is concerned. According to an embodiment of the invention, the system has at least one signal sender unit for sending a signal and a signal receiver unit for receiving the converted signal, which units are arranged on the control module, and at least two signal converter units for converting or converting and reflecting the signal, said signal converter units being arranged on different positions, in particular on different sides, of the device.

Figure 3:
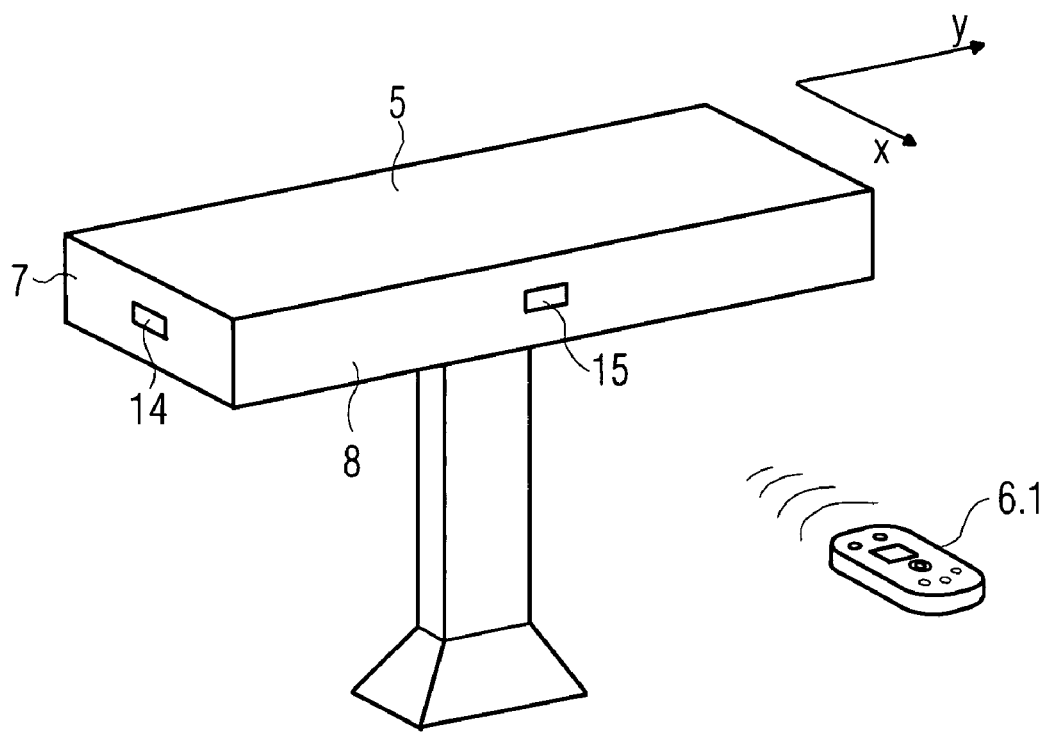
FIG. 3 a perspective view of an adjustable device with RFID transponders.

According to an embodiment of the invention, FIG. 3 shows RFID transponders provided on the sides of the patient couch 5 as signal converter units, wherein a first transponder 14 is arranged on a first side 7 of the patient couch 5, a second transponder 15 is arranged on a second side 8 etc., so that transponders 14, 15 that differ from each other are arranged on different sides. The different transponders differ from each other in the information stored. Accordingly, in this embodiment the control module 6.1, according to a first alternative, said module being provided to operate the patient couch 5, has a so-called RFID reader 18—shown in FIG. 4—as the signal sender and receiver unit.

In principle the RFID communication functions as follows. The RFID reader 18 generates an electromagnetic (U)HF field, which is received by an antenna integrated in the respective transponder (an antenna, an analogue circuit for receiving and sending=transponder, and also a digital circuit and a permanent memory). As soon as the antenna coil comes into the vicinity of the electromagnetic field, an induction current occurs in the antenna coil. Said induction current activates the microchip in the transponder. Once the microchip is activated, it receives commands from the RFID reader 18. The transponder, by modulating a response into the field emitted by the RFID reader 18, sends, for example, data requested by the RFID reader. Thereby the transponder itself does not send a field but just alters the electromagnetic field of the RFID reader by so-called load modulation, by using up the energy of the field, and the RFID reader then detects this.

Figure 4:
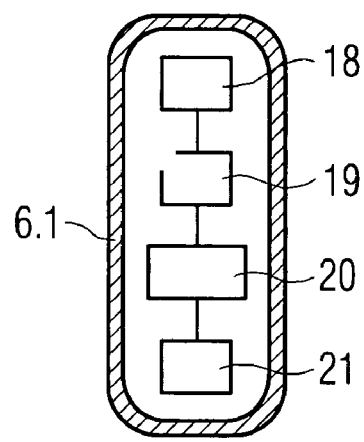
FIG. 4 an interior view of a portable control module according to the invention for operating the adjustable device according to FIG. 3.

FIG. 4 shows an interior view of the control module 6.1 according to a first alternative with the RFID reader 18, a control and processing unit 19, a memory 20 and a communication unit 21. Using the communication unit 21 the control module 6.1 receives commands and data from the system control device 13, for example by radio or WLAN and can also itself send data to the system control device 13. The control and processing unit 19, for example a processor, is provided to control commands and process data. The different operating configurations, for example, can be stored in the memory 20.

Thus the control module 6.1 according to a first alternative or its RFID reader 18 generates a UHF field. If the control module 6.1 according to a first alternative is in front of the first side 7 of the patient table, then the signal is modulated by the first transponder 14. The RFID reader 18 detects the modulated field and reads out the information sent to it relating to the position, in this case, therefore, the first position 9.

The control and processing unit 19 of the control module 6.2 evaluates the information and sets the operating configuration that is appropriate for operation in the first position 9. If the control module 6.1 according to a first alternative is in front of the second side 8 of the patient table, then the signal is modulated by the second transponder 15 and the operating configuration appropriate for operation in the second position 10 is set accordingly. This applies accordingly also for the remaining sides of the patient table 5.

Near-field transponders can be used to avoid superimposition of the signals from different transponders. But it is also possible to assess superimposed response signals with respect to their strength so as to filter out the correct response signal.

Figure 5:
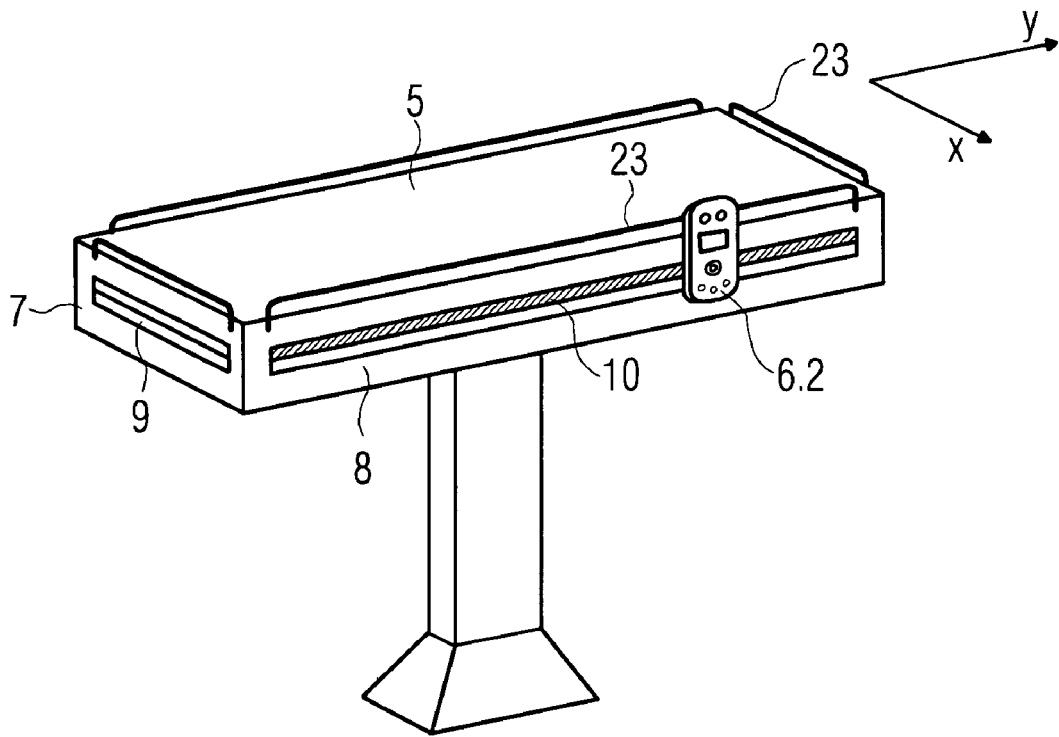
FIG. 5 a perspective view of an adjustable device with optical markings.

In accordance with an embodiment of the invention FIG. 5 shows markings provided on the sides of the patient couch 5, whereby a first marking is arranged on a first side 7 of the patient couch 5, a second marking on a second side 8 etc., so markings that differ from each other are arranged on different sides. The markings can be, for example, removable adhesive strips. The adhesive strips can differ from each other such that they reflect and/or diffract and/or absorb light in different ways.

Thus, for example, the first marking can be made up of two adhesive strips, whereby the first strip reflects light and the second strip absorbs light, whereas the second marking is made up of two adhesive strips which both reflect light in the same way. Moreover, the patient couch 5 has an edge railing 23 on all four sides, to which the control module 6.2 can be attached. The control module 6.2 in question here is radio operated, and can be attached to the table side.

Figure 6:
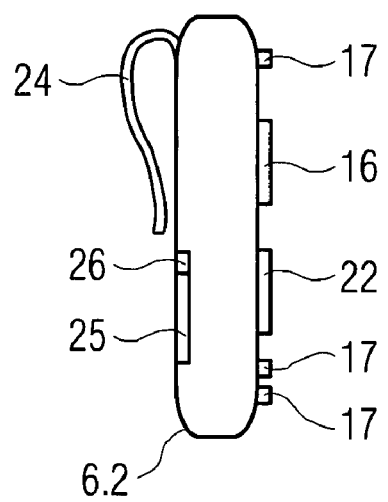
FIG. 6 a side view of a portable control module according to the invention for operating the adjustable device according to FIG. 5.

The control module 6.2 in a second alternative—shown in side view in FIG. 6—contains an optical sensor 25 and a light source 26 for emitting an optical pulse. The control module 6.2 in a second alternative sends a light pulse to the patient couch 5 by means of the light source 26. If the light pulse hits one of the markings, then a corresponding bit pattern according to the adhesive strips is reflected to the control module 6.2 in a second alternative and measured by the optical sensor 25. In the case of two adhesive strips, the bit pattern is binary; in the example mentioned, the first reflected bit pattern is one-zero and the second bit pattern one-one. Depending on which bit pattern is received, the operating configuration of the portable control module 6.2 in a second alternative is then set, thus, for example in the case of the bit pattern one-zero the operating configuration for the first side and in the case of the bit pattern one-one, the operating configuration for the second side.

The control module 6.2 in a second alternative has, in addition, a clip 24, with which it is attached to the railing 23 of the patient table 5. Said control module 6.2 can be hung anywhere on the railing 23 as the user wishes. The control module 6.2 has, in addition, depending on the design several control buttons 17, several operating element 22 and a display 16.

According to a further embodiment of the invention, the C-arm 2 of the x-ray device 1 is adjustable by means of a control module, thus also, for example translationally in a first spatial direction x and a second spatial direction y and/or said C-arm can be rotated around a rotation centre between the x-ray source 3 and the x-ray image recorder 4. These displacements can be implemented, for example by a robotic arm, to which the C-arm 2 is attached. According to the invention, there are also arranged on the C-arm 2 different markings or different transponders on different sides and with their support it is possible to set the operating configuration of the control module controlling the C-arm 2.

The invention can be summarized in brief as follows: to facilitate an intuitive operation of an adjustable device of a medical apparatus, a system for the automatic setting of an operating configuration of the portable control module controlling the adjustable device is provided, wherein different operating configurations in respect of the control of the movement of the movable device differ as far as the relative spatial position of the adjustable device to the control module is concerned. In particular, the system has at least one signal sender unit for sending a signal, said signal sender unit being arranged on the control module, at least two signal converter units for converting and retransmitting or for converting and reflecting the signal, said signal converter units being arranged on different positions on the device, and a signal receiver unit for receiving the converted signal, said signal receiver unit being arranged on the control module.

The invention claimed is:

1. A medical apparatus, comprising:
   an adjustable device;
   a portable control device that controls a movement of the adjustable device;
   a signal sender unit arranged on the control device that sends a signal;
   a plurality of signal converter units arranged on different positions of the adjustable device that convert and retransmit the signal, wherein the different positions for the plurality of signal converter units include at least a first side of the adjustable device and at least a second side of the adjustable device, wherein the first and second sides are mutually perpendicular to one another, wherein the plurality of signal converter units are configured to process the signal from the sender unit so that a directional control by the control device with respect to the adjustable device, as perceived by the user, remains spatially unchanged regardless of whether the user is facing the first or the second side of the adjustable device; and
   a signal receiver unit arranged on the control device that receives the converted signal for setting an operating configuration of the control device to provide said directional spatial control in the control device.

2. The medical apparatus as claimed in claim 1, wherein the signal sender unit and the signal receiver unit comprise an RFID reader.

3. The medical apparatus as claimed in claim 2, wherein the signal converter units comprise RFID transponders.

4. The medical apparatus as claimed in claim 1, wherein the signal sender unit comprises an optical sender unit and the signal receiver unit comprises an optical sensor.

5. The medical apparatus as claimed in claim 4, wherein the signal converter units comprise markings selected from the group consisting of: optically reflecting, optically refracting, and optically absorbing.

6. The medical apparatus as claimed in claim 5, wherein the markings are adhesive strips.

7. The medical apparatus as claimed in claim 1, wherein the signal converter units are detachable.

8. The medical apparatus as claimed in claim 1, wherein the adjustable device is a patient table.

9. The medical apparatus as claimed in claim 8, wherein the patient table comprises an at least two-dimensionally adjustable tabletop.

10. The medical apparatus as claimed in claim 1, wherein the adjustable device is an adjustable C-arm of an x-ray device.

11. The medical apparatus as claimed in claim 1, wherein the portable control device is a joystick or a remote operating unit.

12. A method for automatically setting an operating configuration of a portable control device controlling an adjustable device of a medical apparatus, comprising:
    sending a signal from the portable control device to the adjustable device;
    positioning a plurality of signal converter units on at least a first side of the adjustable device and on at least a second side of the adjustable device, wherein the first and second sides are mutually perpendicular to one another;
    converting the signal into a response signal by a plurality of signal converter units arranged on the adjustable device, wherein the response signal is configured so that a directional control by the control device with respect to the adjustable device, as perceived by the user, remains spatially unchanged regardless of whether the user is facing the first or the second side of the adjustable device;
    receiving the response signal by the portable control device; and
    setting the operating configuration of the portable control device to provide said directional spatial control based on the response signal.

13. The method as claimed in claim 12, wherein the setting is carried out automatically when the medical apparatus or the control device is in operation.

14. The method as claimed in claim 12, wherein the setting is carried out automatically at a regular period of time.

15. The method as claimed in claim 12, wherein the signal is a radio signal or an optical signal.

16. The method as claimed in claim 15, wherein the optical signal is converted and reflected by markings arranged on different sides of the adjustable device that are selected from the group consisting of: reflecting, refracting, and absorbing.

* * * * *